United States Patent
Bordo et al.

(10) Patent No.: US 8,771,490 B2
(45) Date of Patent: Jul. 8, 2014

(54) ELECTROCHEMICAL SENSOR

(75) Inventors: Mark William Bordo, McDonald, PA (US); Wenfeng Peng, Moon Township, PA (US)

(73) Assignee: Industrial Scientific Corporation, Oakdale, PA (US)

( * ) Notice: Subject to any disclaimer, the term of this patent is extended or adjusted under 35 U.S.C. 154(b) by 83 days.

(21) Appl. No.: 12/843,309

(22) Filed: Jul. 26, 2010

(65) Prior Publication Data
US 2012/0018303 A1    Jan. 26, 2012

(51) Int. Cl.
*G01N 27/26*    (2006.01)

(52) U.S. Cl.
USPC ............................ 204/431; 204/409; 204/412

(58) Field of Classification Search
USPC .......... 204/410, 411, 421–429; 409/406–412, 409/415, 421–429, 431, 432; 205/781, 205/783.5–785, 787; 73/23.31, 23.32
See application file for complete search history.

(56) References Cited

U.S. PATENT DOCUMENTS

| | | | |
|---|---|---|---|
| 4,406,770 A * | 9/1983 | Chan et al. .................... | 204/406 |
| 4,587,003 A | 5/1986 | Tantram et al. | |
| 5,914,019 A * | 6/1999 | Dodgson et al. .............. | 204/415 |
| 6,402,933 B1 * | 6/2002 | Dowling ....................... | 205/725 |
| 7,534,333 B2 | 5/2009 | Khalafpour et al. | |
| 7,736,479 B2 | 6/2010 | Prohaska et al. | |
| 2004/0128823 A1 * | 7/2004 | Mole ............................ | 29/592.1 |
| 2010/0170795 A1 * | 7/2010 | Cowburn et al. ............. | 204/406 |

* cited by examiner

*Primary Examiner* — Luan Van
*Assistant Examiner* — Maris R Kessel
(74) *Attorney, Agent, or Firm* — Pepper Hamilton LLP

(57) ABSTRACT

An electrochemical sensor having at least two electrodes, and a reservoir chamber containing electrolyte. The reservoir chamber is internally coated with a wicking material to spread the electrolyte evenly over the walls of the reservoir.

20 Claims, 3 Drawing Sheets

ELECTROCHEMICAL SENSOR

BACKGROUND OF THE INVENTION

Electrochemical sensors are an importance devices in industrial safety, environmental and emissions monitoring, quality and process control and clinical diagnostic applications. They are sensitive, accurate, and low cost, and are used in many portable instruments as well as fixed systems.

Each sensor includes at least two electrodes and an electrolyte. The electrolyte can be an aqueous solution of an acid, an alkali, or a mineral salt; examples are sulfuric acid, phosphoric acid, potassium hydroxide, lithium chloride, and lithium perchorate. The electrolyte can also be of an organic type such as tetraethylammonium perchlorate (TEAP) in a low vapor pressure organic solvent. Because the volume of the electrolyte can change with time and with environmental conditions, a reservoir chamber is usually incorporated into the sensor to provide additional amounts of electrolyte and/or to allow for expansion of the electrolyte in certain environments.

For example, an aqueous electrolyte can lose water to the atmosphere when the relative humidity is low, and absorb water from the atmosphere when the relative humidity is high. The volume of the electrolyte therefore fluctuates with ambient conditions. If the relative humidity is held constant, the electrolyte will adjust its volume and concentration until equilibrium is reached with the surrounding atmosphere.

In order to use the electrolyte in the reservoir, a wick is typically employed inside the sensor cell, disposed in contact with both the electrolyte in the reservoir and the electrolyte between the electrodes. The wick draws the liquid electrolyte and transports it by capillary action. Because electrolyte is free to flow inside the reservoir chamber, some sensors have an adsorbent pad installed in the reservoir to immobilize the electrolyte.

Sensors including wicks are disclosed, for example, in U.S. Pat. Nos. 4,587,003 and 7,534,333, both assigned to City Technology Limited, and incorporated herein by reference.

Commercially available gas sensors typically have a wick. Examples of such gas sensors include the 4 Series toxic gas sensors from City Technology Ltd. in the UK, and the 6A-CO and 6A-$H_2$S sensors from Industrial Scientific Corporation in the US. Most available sensors have a wick that reaches an area in which the electrolyte is most likely to reside.

Current portable instruments are required to be small and convenient to carry. They are often limited in size, however, by the size of the sensors used therein. When sensors are small, the electrolyte reservoir is proportionally reduced in size. In such miniature sensors, it is not practical to place an adsorbent pad in the reservoir as it not only takes up the very limited free space, but also competes with the adsorbent material in the electrode stack for the limited volume of electrolyte. Without an adsorbent pad in the reservoir, however, the electrolyte tends to stay in corners due to surface tension, and loses contact with the wick that is required to transport the electrolyte. As a consequence, the electrode stack can dry out, even though there is a sufficient amount of electrolyte left in the reservoir, and when this occurs, the sensor has either no or low sensitivity, and/or long response times to the analyte of interest.

SUMMARY OF THE INVENTION

It is therefore the object of the invention to provide a miniature sensor that delivers reliable performance under varying environmental conditions.

It is a further object of the invention to provide a miniature sensor that is robust and easy to manufacture.

To accomplish these and other objects, the invention is directed to a miniature sensor in which is incorporated a small reservoir chamber that is internally coated with a wicking material which has an affinity to the electrolyte and is chemically stable. The wicking material provides a connection between electrolyte in the reservoir and electrolyte in the electrode stack.

In particular, the invention is directed to an electrochemical sensor comprising a housing including an opening for admitting gas for analysis, an electrode stack disposed within the housing, and comprising at least two electrodes separated by an electrolyte-absorbent separator (typically fiberglass) placed therebetween, a reservoir for electrolyte disposed adjacent the electrolyte stack, the reservoir being defined by walls, and a wicking material coating on the walls of the reservoir, the wicking material coating being constructed and arranged for spreading electrolyte evenly over the walls of the reservoir.

DETAILED DESCRIPTION OF THE INVENTION

Figure 1:
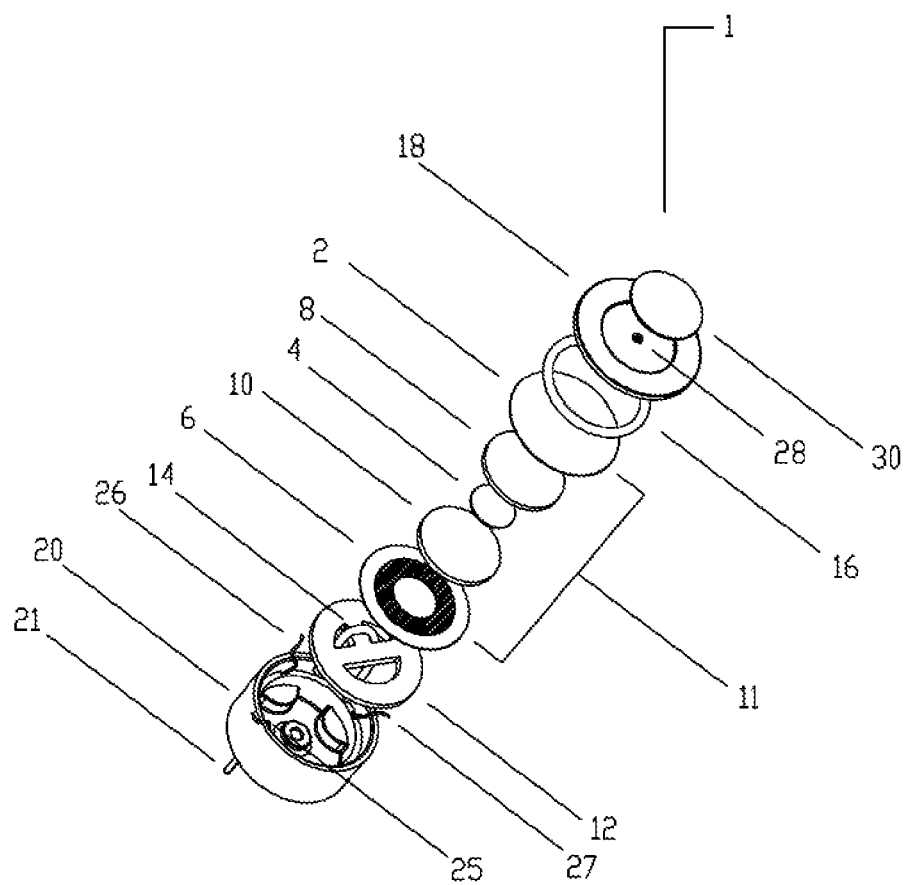
FIG. 1 is an exploded view of an electrochemical gas sensor according to the invention, which includes an electrode stack, an electrode reservoir chamber and a wick between therebetween.
Figure 2:
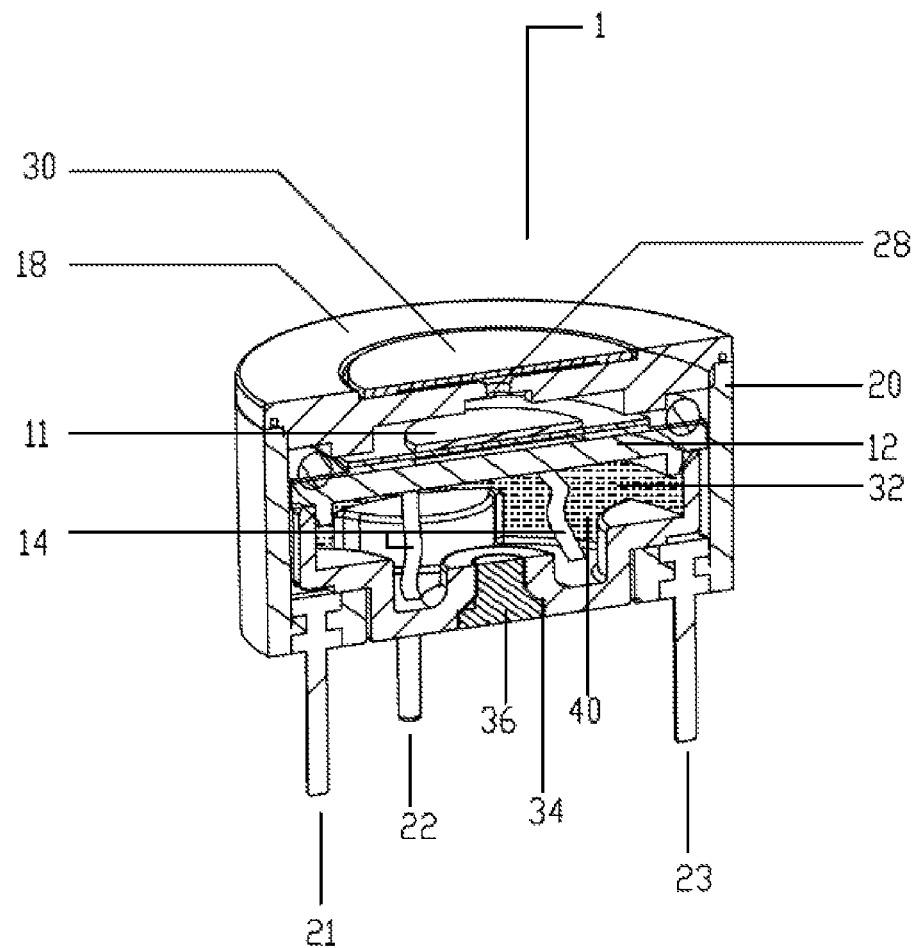
FIG. 2 is lateral cross-sectional view of the sensor of FIG. 1.

With reference to FIGS. 1 and 2, an electrochemical sensor 1 contains three electrodes, a working electrode 2, a reference electrode 4 and a counter electrode 6. These electrodes are separated by separators 8 and 10, with separator 8 between working electrode 2 and reference electrode 4, and separator 10 between reference electrode 4 and counter electrode 6. The electrodes 2, 4, 6 and separators 8 and 10, which is referred to as an electrode stack 11, is supported on a slotted plastic disk 12, an insulating support, which has a wick 14 extending downwardly. The electrode stack 11, with support disk 12 on one surface thereof and O-ring 16 on the other surface thereof, is housed in a plastic enclosure formed by attaching a cap 18 to a sensor housing 20, typically by ultrasonic welding.

As can be seen more clearly in FIG. 2, the plastic housing 20 has three external electrical connector pins 21, 22, 23 molded in. Within the housing, there are three metal wires or strips 25, 26, and 27 connected to the pins 21, 22, and 23, respectively, at one end thereof, and the three wires or strips 25, 26 and 27 are connected to the three electrodes 2, 4 and 6, respectively, at the other end thereof.

Under the support disk 12 is an electrolyte reservoir 32, with a vent 34. After electrolyte is filled into the reservoir through the 34, vent is plugged with a plastic insert 36.

The wick 14 maintains physical contact with both the electrode stack 11 through the slotted disk 14, and the inner surface of the reservoir chamber 32. The wick 14 wicks up electrolyte from the reservoir and wets the separators 8 and 10 in the electrode stack 11.

Figure 3:
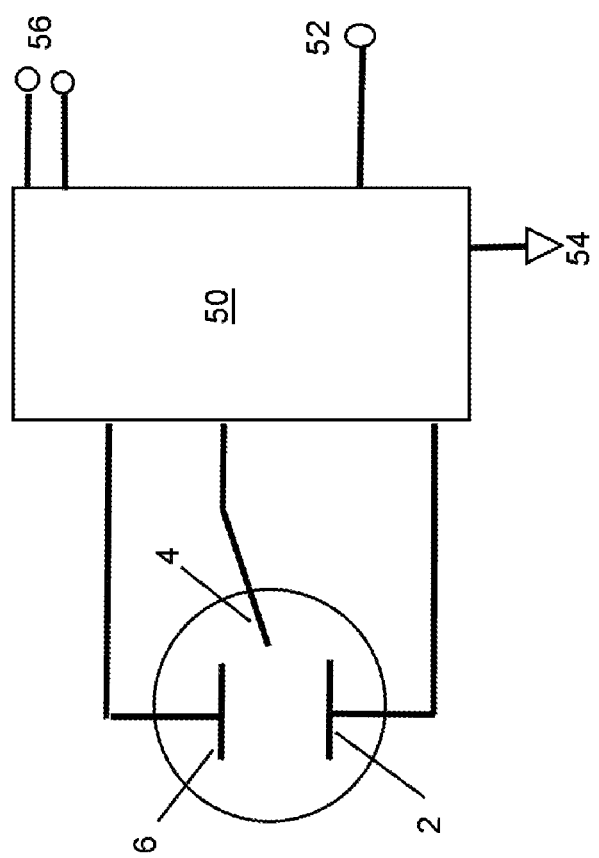
FIG. 3 is a schematic diagram of the electrochemical gas sensor according to the invention, connected to a potentiostat circuit.

As shown in FIG. 3, when the three electrodes 2, 4 and 6 are connected to a potentiostat circuit 50 with an appropriate bias voltage, the sensor is ready to work. The target gas enters the sensor through capillary 28 in cap 18, and electrochemical reactions take place within the stack 11 generating a current output at the working electrode, which is amplified by the potentiostat circuit, and detected at output 52. The potentiostat circuit is well known in the art, and includes ground 54 and a connection 56 to a power source.

The capillary 28 is protected from dust and moisture by a porous membrane 30.

When the overall size of the sensor is small, for example a cylinder 5-15 mm in diameter×5-15 mm in height, the electrolyte reservoir 32 is also small, for example in the range of 0.3-1 ml in volume. With projections in the areas of pins 21, 22 and 23, and the vent 34 in the bottom of the reservoir, the reservoir has many small corners that easily trap the electrolyte, and due to surface tension, the small amount of liquid electrolyte is difficult to spread over the whole surface of the bottom of the reservoir. The amount of electrolyte in the reservoir is also quite small, for example in the range of 0.10-0.15 ml, typically 0.12 ml.

The sensor may also be in the shape of a cuboid, of a size, for example, 5-15 mm in each of length, width and height.

While the invention is especially advantageous with respect to such miniature sensors, it is not limited to miniature sensors, and may be used with sensors of all sizes and shapes.

The electrode stack 11 is the heart of the sensor in which electrochemical reactions take place. The separators 8 and 10 must be charged with electrolyte at all times in order to keep the sensor in operating condition. If there is not enough electrolyte, the ionic conductivity between electrodes will be poor and the sensor will not function properly, for example exhibiting a long response time and low output.

According to the invention, the surface of the reservoir is coated with a wicking material 40; when there is an excess of electrolyte in the reservoir, it is spread over the whole surface of the reservoir by the wicking material 40. The wicking material is in physical contact with the surface of the reservoir, and will therefore wick up electrolyte to the electrode stack 11, and keep the sensor in operating condition. The wicking material 40 also assists in the filling process, as it wicks the electrolyte away from the vent, where the electrolyte might otherwise block the vent during the filling process, and/or remain in the vent area and prevent further filling.

A large variety of materials may be used for the wicking material coating. For example, fiberglass paper may be crushed into particles, and dispersed in water to form a colloid and dried. Other suitable materials include fumed silica ($SiO_2$), powdered alumina ($Al_2O_3$), titania ($TiO_2$), zirconia ($ZrO_2$), and other ceramic materials and mixtures thereof. Carbon powder and absorbent polymers, such as polypropylene and polyethylene in fiber form may also be used. The wicking material must be compatible with the electrolyte, and be chemically stable.

When the wicking material coating in the reservoir is in physical contact with the electrolyte in the electrode stack, the wick may be omitted.

While the disclosed embodiment shows the reservoir arranged below the stack, other arrangements, for example by the side of the stack, above the stack, or even within the stack (between the electrodes) may be used.

EXAMPLES

Example 1

0.5 g of a Whatman GF/A binder-free, glass microfiber filter disk is crushed at 10,000+ lbs, dispersed in 100 mL water, and then mixed to form a colloid. About 0.5 ml of the colloid is injected into a 0.5 ml electrolyte reservoir and allowed to dry at 60° C. for 1 hr. The colloid is evenly distributed and uniformly coated the internal walls of the reservoir. The coating adheres strongly to the walls. When the reservoir is filled with 0.15 ml diluted sulfuric acid electrolyte, it absorbs a minimal amount of the electrolyte and spreads it quickly over the entire surface of the coated area.

The reservoir is deployed in a sensor to detect carbon monoxide gas.

Example 2

0.3 g of fumed silicon dioxide ($SiO_2$), 99.5%, 400 mesh from Alfa Aesar, US, is added to 100 ml of de-ionized water and then mixed at room temperature to form a colloid. About 0.3 ml of the mixture is injected into a 0.3 ml electrolyte reservoir and then allowed to dry at 50° C. A uniform coating is formed on the internal walls of the reservoir. The reservoir is filled with 0.1 ml of diluted phosphoric acid ($H_3PO_4$) electrolyte, and deployed in a sensor to detect hydrogen sulfide gas.

What is claimed is:

1. A method of preparing an electrochemical sensor comprising the steps of:
   providing a sensor housing, said housing including an opening, an electrode stack disposed within the housing, at least two electrodes separated by an electrolyte-absorbent separator disposed between said at least two electrodes, and a reservoir for receiving and electrolyte and having an inner surface said reservoir being disposed adjacent the electrodes;
   preparing a colloidal dispersion of a wicking material;
   coating the inner surface of the reservoir with said colloidal dispersion; and
   drying said coating of said colloidal dispersion;
   wherein an electrolyte introduced into the reservoir is spread evenly over the inner surface of the reservoir.

2. The method according to claim 1, wherein the wicking material comprises at least one material selected for the group consisting of fiberglass, fumed SiO2, Al2O3, TiO2, and ZrO2.

3. The method according to claim 1, further comprising extending the coating from the reservoir to the electrode stack.

4. The method according to claim 1, wherein the inner surface of the reservoir is uniformly coated with said colloidal dispersion.

5. The method according to claim 1, wherein the colloidal suspension is prepared using a liquid selected from the group consisting of water, a salt solution, an organic solvent, and combinations thereof.

6. The method according to claim 2, wherein the polymer is an absorbant polymer.

7. The method according to claim 2, wherein the absorbant polymer is polypropylene or polyethylene.

8. An electrochemical sensor produced according to the steps of:
   providing a sensor housing and an electrode stack that is disposed within the sensor housing, said electrode stack including at least two electrodes and an electrolyte-absorbent separator that is disposed between said at least two electrodes, said sensor housing having surfaces that define a reservoir chamber for containing an electrolyte;
   preparing a colloid of a wicking material in a liquid, said wicking material having an affinity for the electrolyte contained in the reservoir chamber, said wicking material being chemically stable in the presence of the electrolyte;

placing the colloid in the reservoir; and drying the colloid to cause the wicking material component of the colloid to adhere to the surfaces of the reservoir chamber and form a coating of wicking material thereon, said coating of wicking material adhering to the surfaces of the reservoir chamber and uniformly coating the walls of the chamber, the electrolyte in the reservoir chamber spreading over the surface of the coated walls of the reservoir chamber.

9. The electrochemical sensor according to claim 8 wherein the wicking material is selected from the group comprising particles of fiberglass and other ceramic materials.

10. The electrochemical sensor according to claim 9 wherein the wicking material is selected from the group comprising fumed silica, powdered alumina, titania, zirconia and mixtures thereof.

11. A new gas analysis device comprising;

a sensor produced according to the steps of;

providing a sensor housing and an electrode stack that is disposed within the sensor housing, said electrode stack including at least two electrodes and an electrolyte-absorbent separator that is disposed between said at least two electrodes, said sensor housing having surfaces that define a reservoir chamber for containing an electrolyte;

preparing a colloid of a wicking material in a liquid, said wicking material having an affinity for the electrolyte and being chemically stable in the presence of the electrolyte;

placing the colloid in the reservoir; and drying the colloid in the reservoir to cause the wicking material component of the colloid to adhere to the surfaces of the reservoir chamber and form a coating of wicking material thereon, said wicking material forming a uniform coating that adheres to the surfaces of the reservoir chamber, such that electrolyte in the reservoir chamber spreads throughout the coating of wicking material; and a potentiostat circuit that is connected to the electrodes of the sensor, said potentiostat circuit providing a biasing voltage that is sufficient to generate a current at one of the electrodes when a gas to be determined is present.

12. A new gas analysis device according to claim 11, additionally comprising a power source.

13. An electrochemical sensor comprising:

a housing that defines an opening for admitting gas for analysis:

an electrode stack that is disposed within the housing, said electrode stack including at least two electrodes with an electrolyte-absorbent separator located between the two electrodes;

a reservoir having walls that define a chamber, said chamber containing a supply of electrolyte;

a wicking material that adheres to the walls of the chamber, said wicking material being in the form of a coating, said wicking material uniformly coating the walls of the chamber and having an affinity for said electrolyte such that said coating of wicking material spreads said electrolyte over the surface of the coated area of the internal walls of the reservoir; and a wick that is in contact with said electrode stack and with said coating of wicking material to wet the separator in the electrode stack with electrolyte from the reservoir.

14. The sensor according to claim 13 wherein the wicking material coating comprises at least one material selected for the group consisting of fiberglass, fumed $SiO_2$, $Al_2O_3$, $TiO_2$ and $ZrO_2$.

15. The sensor according to claim 13 wherein the coating of wicking material is adhered to the walls of the chamber by drying a colloid of said wicking material.

16. The sensor according to claim 15 where the coating of wicking material is comprised of elements of wicking material that remain from said dried colloid.

17. An electrochemical sensor comprising:

a housing that defines an opening for admitting gas for analysis:

an electrode stack that is disposed within the housing, said electrode stack including at least two electrodes with an electrolyte-absorbent separator located between the two electrodes;

a reservoir having walls that define a chamber, said chamber containing a supply of electrolyte; and a wicking material that adheres to the walls of the chamber, said wicking material being in the form of a coating that provides a connection between electrolyte in the reservoir and electrolyte in the electrode stack, said wicking material uniformly coating the walls of the chamber and having an affinity for said electrolyte such that said coating of wicking material spreads said electrolyte over the surface of the coated area of the internal walls of the reservoir chamber and to said electrode stack.

18. The sensor according to claim 17 wherein the wicking material coating comprises at least one material selected for the group consisting of fiberglass, fumed $SiO_2$, $Al_2O_3$, $TiO_2$ and $ZrO_2$.

19. The sensor according to claim 17 wherein the coating of wicking material is adhered to the walls of the chamber by drying a colloid of said wicking material.

20. The sensor according to claim 19 where the coating of wicking material is comprised of elements of wicking material that remain from said dried colloid.

\* \* \* \* \*